United States Patent
Gray et al.

(10) Patent No.: US 8,505,170 B1
(45) Date of Patent: Aug. 13, 2013

(54) ADJUSTABLE LINE CLIP HOLDER

(75) Inventors: Deborah B. Gray, Deland, FL (US); William L. Alexander, Baton Rouge, LA (US)

(73) Assignee: Deborah B. Gray, Deland, FL (US)

( * ) Notice: Subject to any disclaimer, the term of this patent is extended or adjusted under 35 U.S.C. 154(b) by 247 days.

(21) Appl. No.: 13/009,102

(22) Filed: Jan. 19, 2011

Related U.S. Application Data

(63) Continuation-in-part of application No. 29/381,756, filed on Dec. 22, 2010, now Pat. No. Des. 639,937.

(60) Provisional application No. 61/410,379, filed on Nov. 5, 2010.

(51) Int. Cl.
*A44B 6/00* (2006.01)

(52) U.S. Cl.
USPC .......................................................... 24/3.12

(58) Field of Classification Search
USPC .................... 29/817; 24/3.3, 33.5, 343, 3.12, 24/350; 242/388.9
See application file for complete search history.

(56) References Cited

U.S. PATENT DOCUMENTS

| | | |
|---|---|---|
| D32,957 S | 7/1900 | Lewis |
| D34,938 S | 8/1901 | Henderson |
| 754,285 A | 3/1904 | Dick |
| 1,791,696 A | 10/1931 | Alexander |
| 3,266,111 A * | 8/1966 | Abel ................................ 24/3.3 |
| 3,747,166 A | 7/1973 | Eross |
| 3,883,981 A | 5/1975 | Bohn |
| D252,256 S | 7/1979 | Kline |
| D258,138 S | 2/1981 | Wood |
| D284,426 S | 7/1986 | Morris |
| 4,742,824 A | 5/1988 | Payton |
| D300,804 S | 4/1989 | Myers |
| 4,820,274 A | 4/1989 | Choksi |
| 4,836,200 A | 6/1989 | Clark |
| 4,875,718 A | 10/1989 | Marken |
| 4,915,104 A | 4/1990 | Marcy |
| D311,609 S | 10/1990 | Stoneburner |
| 4,979,714 A | 12/1990 | Russell |
| 5,188,609 A | 2/1993 | Bayless |
| 5,222,486 A | 6/1993 | Vaughn |
| 5,284,134 A | 2/1994 | Vaughn |
| 5,308,337 A | 5/1994 | Bingisser |
| 5,438,979 A | 8/1995 | Johnson |
| 5,507,460 A | 4/1996 | Schneider |
| 5,944,696 A | 8/1999 | Bayless et al. |
| 6,394,088 B1 | 5/2002 | Frye |
| 6,526,635 B2 | 3/2003 | Nasu |
| 6,763,832 B1 | 7/2004 | Kirsch |
| 6,804,866 B2 | 10/2004 | Lemke |

(Continued)

*Primary Examiner* — John C Hong

(74) *Attorney, Agent, or Firm* — Brian S. Steinberger; Law Offices of Brian S. Steinberger, P.A.

(57) ABSTRACT

Clips, devices, apparatus and methods of holding and supporting different diameter lines and conduits, such as medical oxygen air lines, earphone or headset wire lines, other types of wires, and power cords, and the like in a clip that can attach to clothing such as to pants, belts and pockets. The clip can include a rear U-shaped base and downwardly and upwardly protruding elongated members having different sets of upper and lower bends. The clip can be formed from a single vinyl coated wire line, that forms three sets of bends, each set having a different diameter. The lines and conduits can be securely held in different diameter sets of bends.

19 Claims, 10 Drawing Sheets

(56) References Cited

U.S. PATENT DOCUMENTS

| | | |
|---|---|---|
| D550,347 S | 9/2007 | Norton |
| D586,258 S | 2/2009 | Guney |
| D588,498 S | 3/2009 | Davidson |
| D639,937 S | 6/2011 | Gray |
| 2007/0056590 A1 | 3/2007 | Wolfson |
| 2008/0042000 A1 | 2/2008 | Horton |
| 2010/0280459 A1 | 11/2010 | Werner |

* cited by examiner

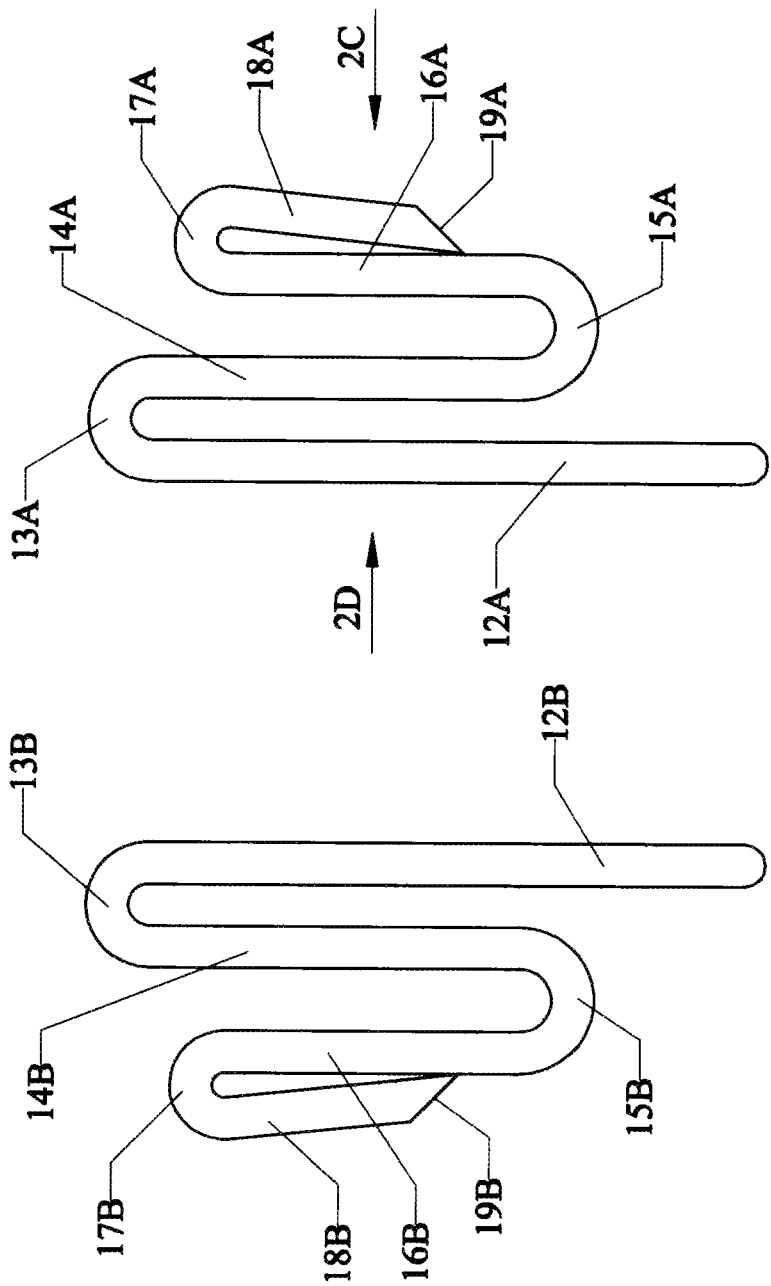

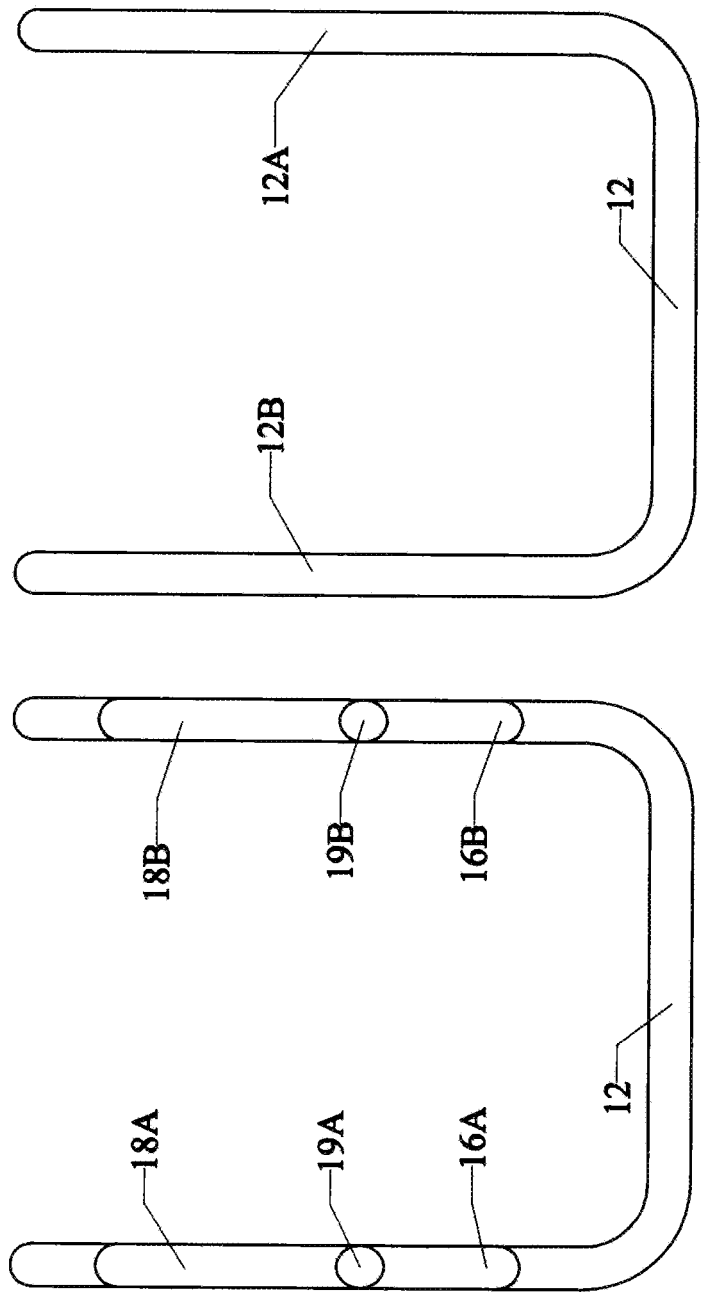

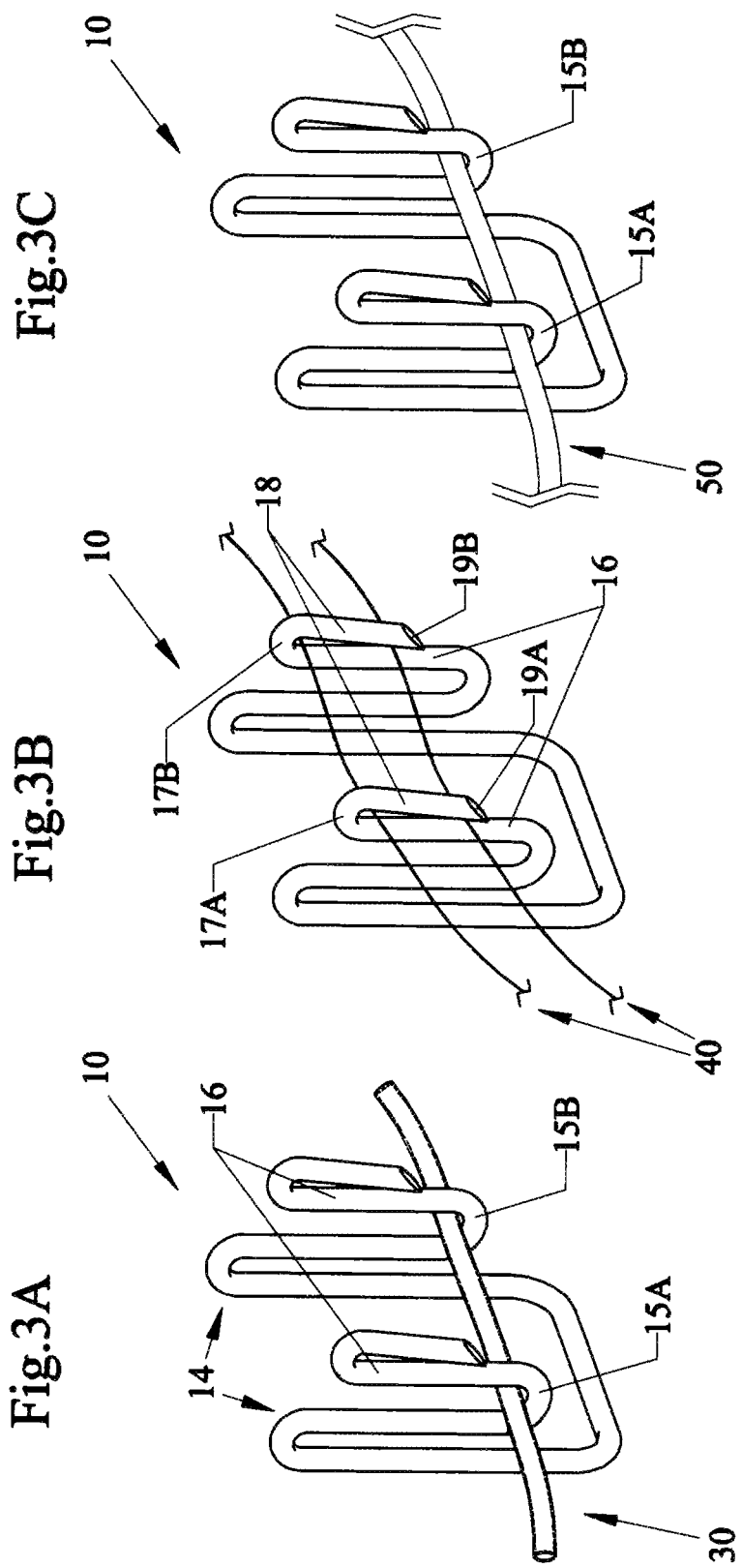

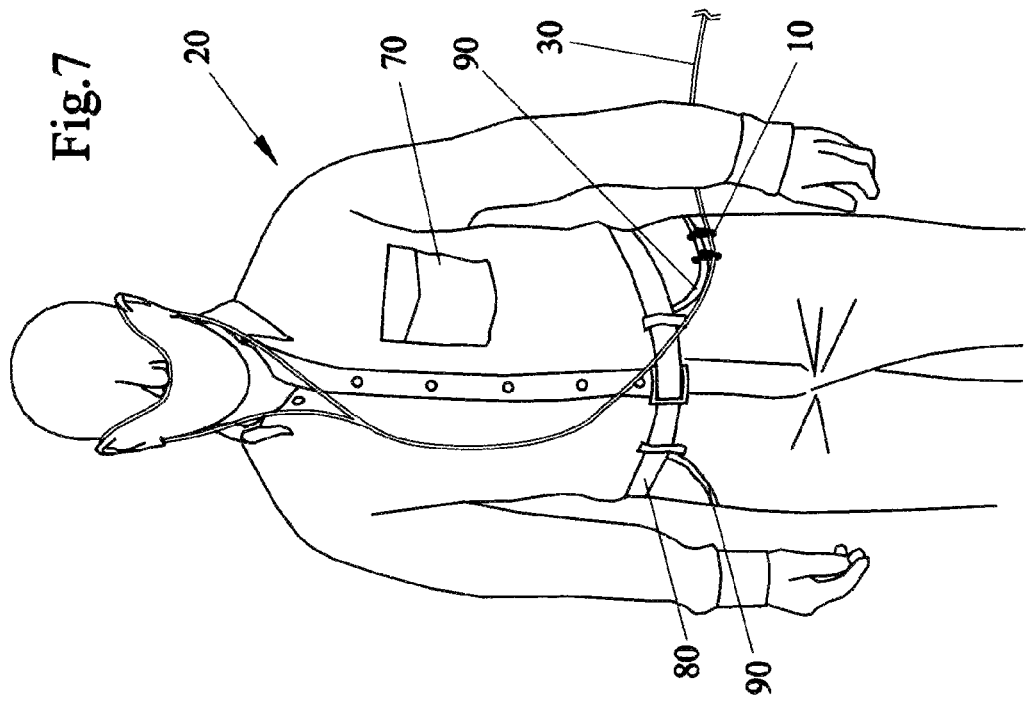
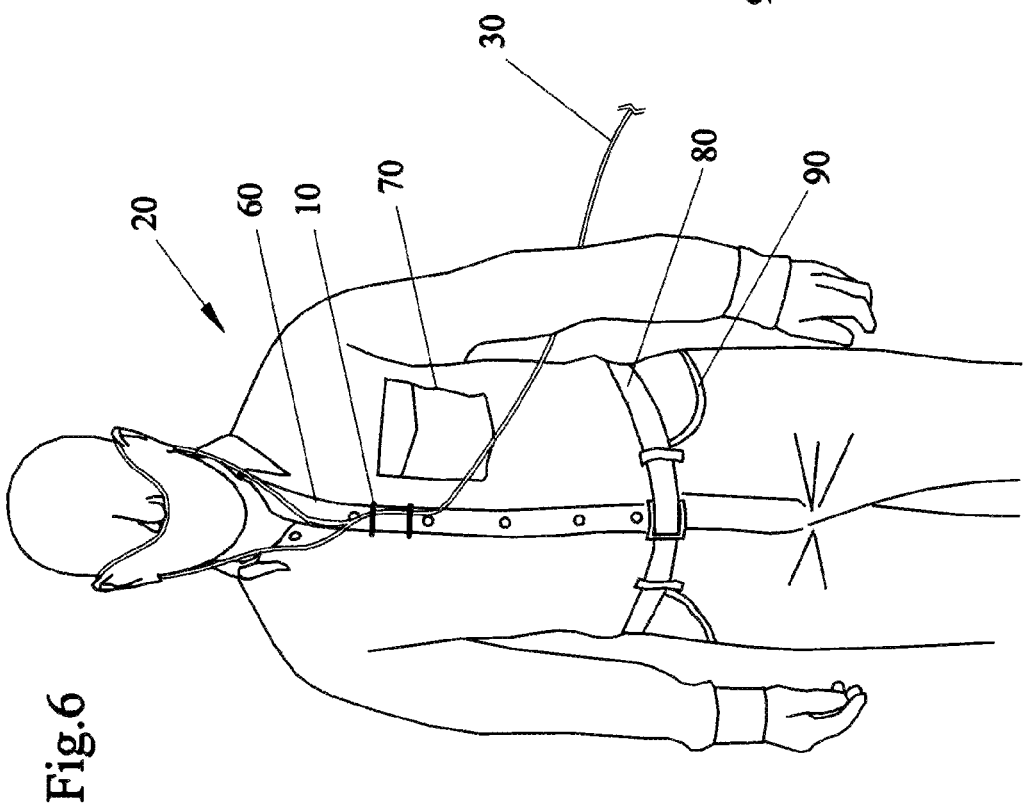

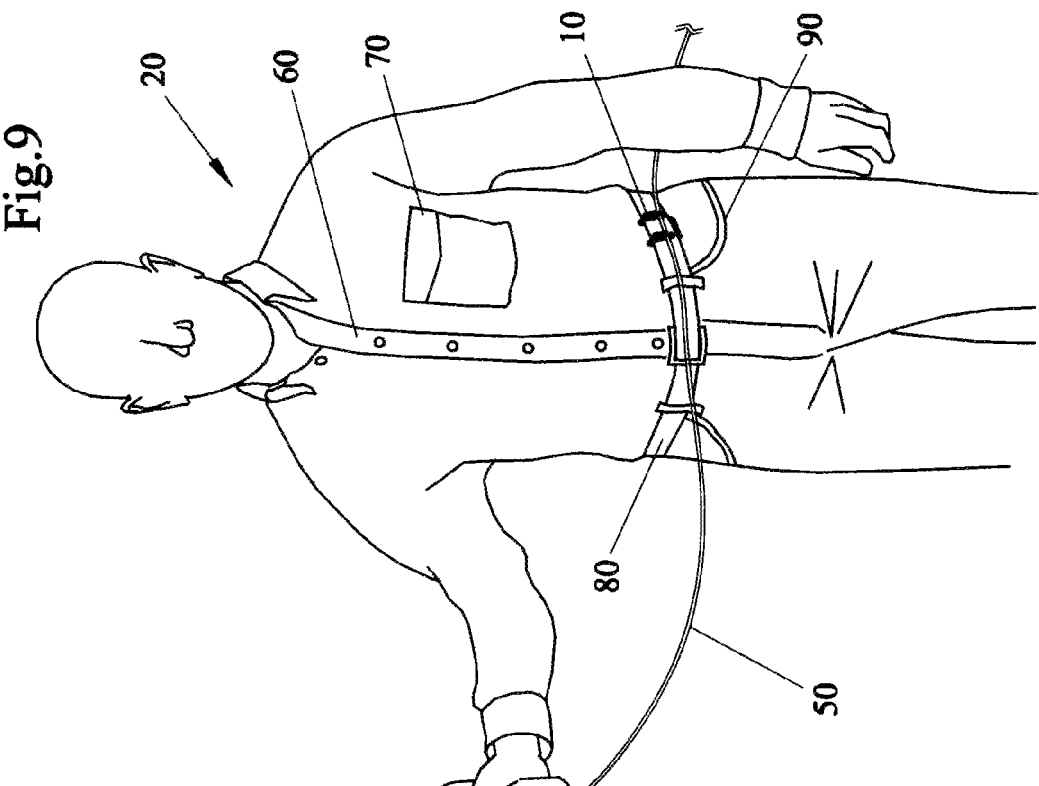
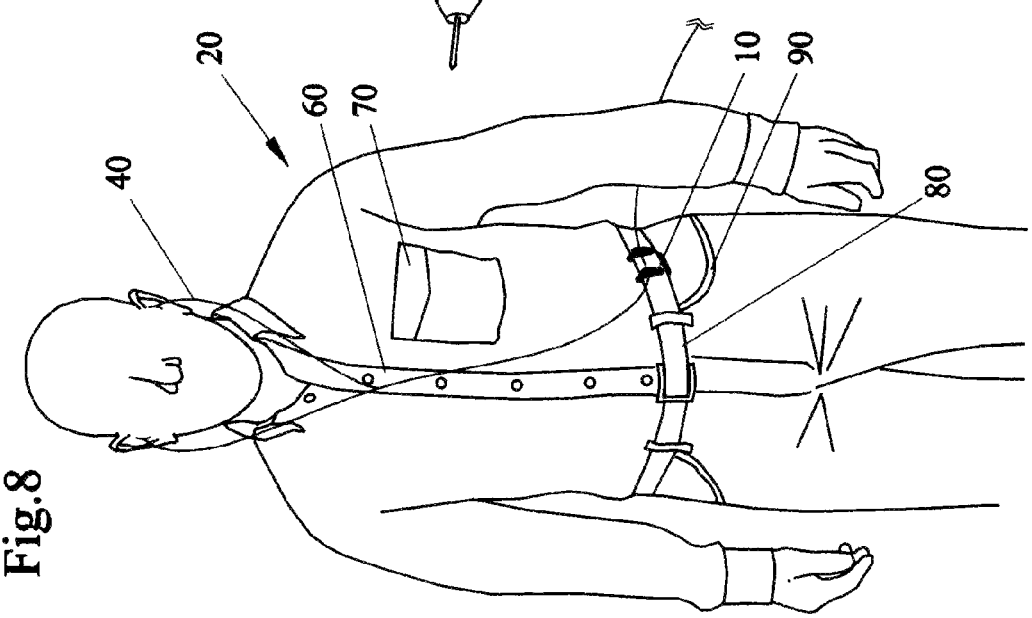

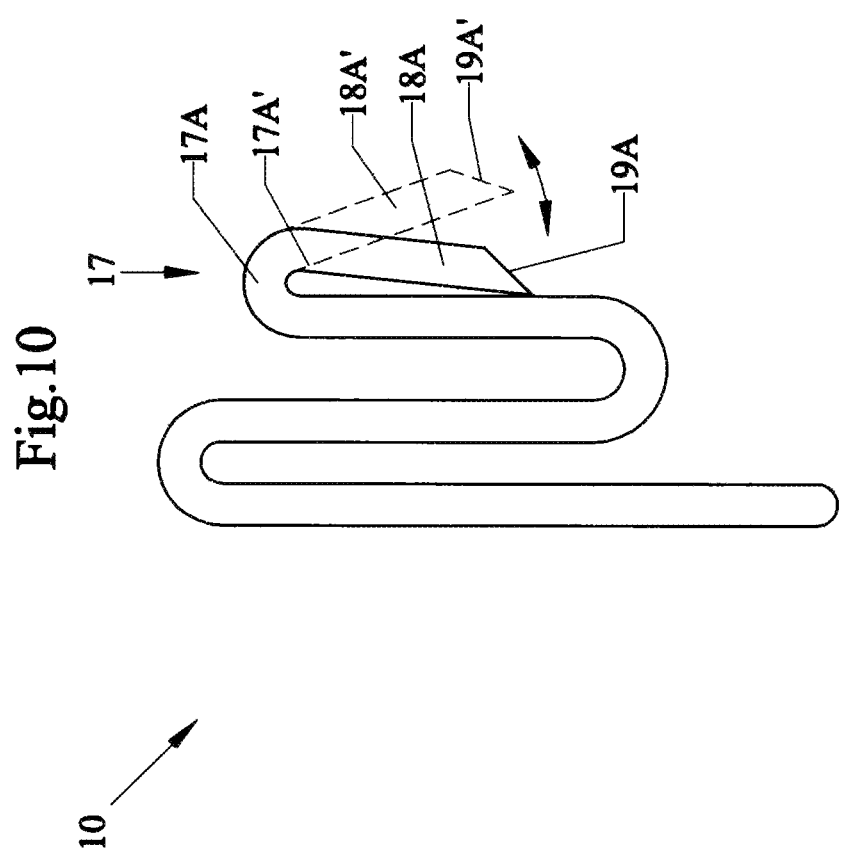

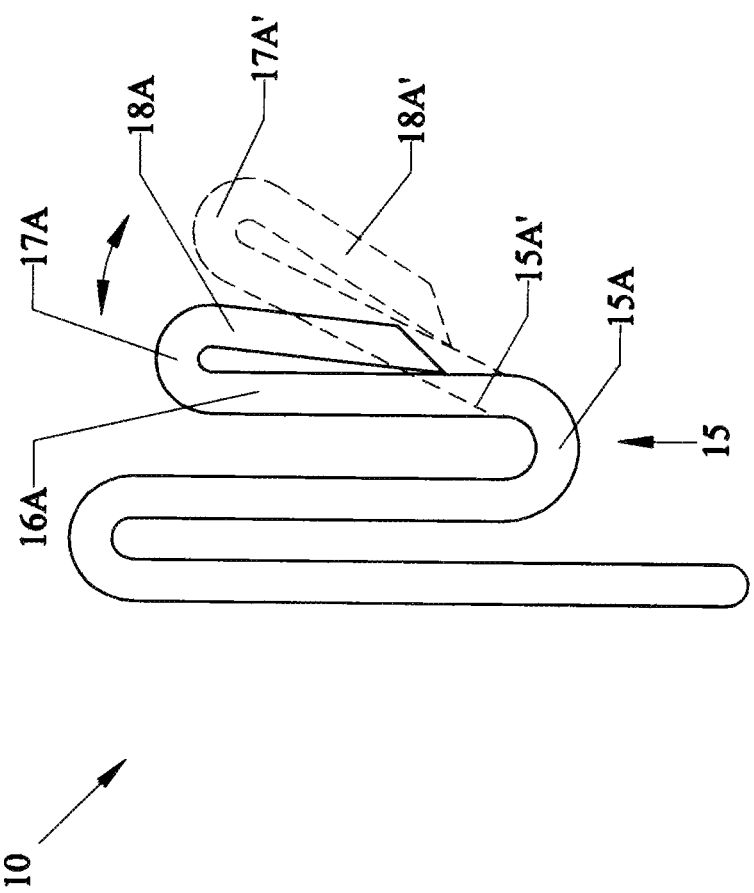

ADJUSTABLE LINE CLIP HOLDER

This invention is a Continuation-In-Part of U.S. Design patent application Ser. No. 29/381,756 filed Dec. 22, 2010, now U.S. Design Pat. D639,937 and this invention claims the benefit of priority to U.S. Provisional Application Ser. No. 61/410,379 filed Nov. 5, 2010.

FIELD OF INVENTION

This invention relates to clips, and in particular to clips, devices, apparatus and methods of holding and supporting different diameter conduits, such as medical air lines, earphone or headset lines, wires, and power cords in a clip that can attach to clothing such as to pants, belts and pockets.

BACKGROUND AND PRIOR ART

Oxygen tubes are often used by a patients that require oxygen or other gases over long periods of time. The tubes generally require a cannula apparatus such as a nasal cannula generally includes an oxygen-carrying tube with two branches capable of being draped over the ears of a patient. Two tubular branches are usually joined together in front of the patient's face with a center part providing two nostril orifices. In order to keep the orifices of the nasal cannula remain in contact with the patient's nostrils in use, the tubular branches of the nasal cannula are often supported by the patient's ears. Here, the tubular branches function as an earpiece to hold the cannula apparatus in place.

However, the extensive use of a nasal cannula often irritates and causes discomfort to the patient. The current nasal cannula apparatuses fail to provide necessary support in relieving the pressure of the cannula from the patient's ears, face, neck, and skin. As a result, discomfort above and behind the patient's ears is a common occurrence. Often the discomfort can start off with a simple redness and progress to sores or ulcerations above the ears due to constant rubbing of the tubing against the skin.

An additional problem occurs with moving patients. Many mobile patients that require the constant administration of oxygen use at least a 50-foot cannula within their homes. Since a longer cannula is required for a freely moving patient, the additional weight from the longer cannula causes a substantial increase in pressure against the skin and areas that support and hold the cannula. Further, the combination of the moving patient and long cannula can often cause the cannula to snag on furniture or other objects located around the patient. To avoid this problem a common practice to alleviate discomfort often will require the patient to physically hold the cannula all the time. However, the patient constantly having to hold the cannula while they move about will limit the patient to only being able to have use of one free hand during the day.

While a patient is resting or sleeping, it is not unusual for the cannula to be accidentally displaced or pulled away from the patient's ears, face, neck, and skin. The displacement and pulling action can aggravate irritations and/or soreness associated with the use of the cannula. Also, if the tubular branches of a nasal cannula are separated from the patient's ears, the nostril orifices can move out of contact with the patient's nostrils and render the cannula ineffective for its intended use and uncomfortable to the patient.

Currently, there are a variety of devices available that attempt to alleviate these problems. Some of these devices do so by removing the cannula from the patient's ears. Other variations of relief include the use of a head cap to support and secure the cannula as well as for securing the cannula to eye glasses. However, by attaching the cannula to eyeglasses or to a skull cap is that the patient cannot comfortably wear the eyeglasses or the skull cap when sleeping. Additionally, skull caps need to be sized for each user.

A device used to prevent irritation generated by a cannula has included a strap-like device adapted to be draped on top of a patient's head. The strap-like devices have two looped ends through which the tubular branches of the cannula are routed. If the length of the strap-like device is appropriately sized, the tubular branches will be suspended above the patient's ears as the strap device is draped across the patient's head.

However, strap-like devices are limited in that when the tubular branches are supported within the ends of the strap-like device, the tubular portions can shift lengthwise relative to the end of the device. Further, a strap-like device does little to alleviate the problem of snagging and pulling of the cannula for the moving patient.

Sometimes ear pads that are placed behind the patient's ears to help alleviate the discomfort of the cannula rubbing against the ear. However, since the pads do not provide a means for controlling the tension and pressure created by a cannula, the pads do not eliminate all the discomfort associated with the use of a cannula. Pads are sometimes placed over areas already irritated by the cannula, which can slow the healing process around that area. Further, these pads must often be replaced, making them an expensive and inefficient technique for overcoming the discomfort caused by a cannula.

Some types of clips for medical tubing have been used to fixed items to beds or clothing. The area for holding the medical tubing is not located along the surface of the clip but rather along an elongate strip attached to the clip. By placing the medical tube holder on a strip and not directly on the clip, such devices are less effective in alleviating the pressure generated by the cannula against the patient's skin and ears because the strip can bend under the weight of the cannula or when the cannula is snagged against an object. Further, a restive sleeping patient can dislodge the cannula, or even the elongate strip, thus rendering the common clip ineffective for its intended purpose.

Another tube/wire holding device designed for maintaining the position of medical tubes is a mesentery tube holder apparatus with a base plate that would adhere to a patient's skin. A flap with one end permanently affixed to the base plate holds a tube by having an opposite end that adheres to a medical tube. Such fasteners can be difficult to use and ineffective in relieving the pressure of the cannula from the ears. Moreover, the adhesives can irritate skin making such devices undesirable for extended use.

Thus, the need exists for solutions to the above problems with the prior art.

SUMMARY OF THE INVENTION

A primary objective of the present invention is to provide clips, devices, apparatus and methods of holding and supporting different diameter conduits, such as medical oxygen air lines in a clip that can attach to clothing such as to pants, belts and pockets.

A secondary objective of the present invention is to provide clips, devices, apparatus and methods of holding and supporting different diameter conduits, such as earphone and headset lines in a clip that can attach to clothing such as to pants, belts and pockets.

A third objective of the present invention is to provide clips, devices, apparatus and methods of holding and supporting different diameter conduits, such as wires in a clip that can attach to clothing such as to pants, belts and pockets.

A fourth objective of the present invention is to provide clips, devices, apparatus and methods of holding and supporting different diameter conduits, such as power cords in a clip that can attach to clothing such as to pants, belts and pockets.

A fifth objective of the present invention is to provide clip holders and methods of holding and supporting medical oxygen lines to patients so the patients can perform daily living activities with ease, without having to fight the oxygen line itself.

A sixth objective of the present invention is to provide clip holders and methods of holding and supporting medical oxygen lines to patients with ear supported cannulas which eliminates sudden painful pulling of the cannulas from the patient's ears.

A seventh objective of the present invention is to provide clip holders and methods of holding and supporting medical oxygen lines to patients with cannulas that keeps the line out of the patient's walking path, resulting in less trips and falls.

An eighth objective of the present invention is to provide clip holders and methods of holding and supporting medical oxygen lines to patients with ear supported cannulas that reduces the weight and pressure and pulling and yanking of the lines on the ears.

A ninth objective of the present invention is to provide clip holders and methods of holding and supporting medical oxygen lines to patients with ear supported cannulas that eliminates weight pressure and constant pull and potential yanking of the lines from the nose connection eliminating soreness and resulting raw skin problems.

A tenth objective of the present invention is to provide clip holders and methods of holding and supporting medical oxygen lines to patients with ear supported cannulas, allowing for both hands of patient to be free for different activities such as daily hygiene activities that can include going to the bathroom, washing hands, brushing teeth, and carrying objects, while supporting the lines out of the way of the patient's hands.

An eleventh objective of the present invention is to provide clip holders and methods of holding and supporting medical oxygen lines to patients with ear supported cannulas by securing the lines to not pull on the patient allowing for better patient sleep.

A twelfth objective of the present invention is to provide clip holders and methods of holding and supporting medical oxygen lines to patients with ear supported cannulas, that can be used with old belts or elastic bands in a shower or bath so that the lines can be safely secured out of the way of the standing or sitting patient taking a shower or bath.

A thirteenth objective of the present invention is to provide clip holders and methods of holding and supporting medical oxygen lines to patients with ear supported cannulas, to safely and comfortably secure the lines allow for the patient to get in and out of vehicles (cars and like) during the day or night, and eliminate any cumbersome or burdensome difficulties while using the lines.

A fourteenth objective of the present invention is to provide clip holders and methods of holding and supporting medical oxygen lines to patients with ear supported cannulas, that can safely and comfortably secured to the left or right side of the patient with belts, elastic bands, fabrics, and virtually any other type of material and clothing.

A fifteenth objective of the present invention is to provide clip holders and methods of holding and supporting different diameter conduit lines to persons, where adjustments can be done using fingers to press the clip portions together or pulled apart, and line length adjustment made by simply sliding the lines to the left or to the right.

A clip holder for holding and securely supporting elongated lines, can include a base member having an upper end and a lower end, a first set of upper bends attached to the upper end of the base member, a first set of prongs downwardly extending from the first set of upper bends, a second set of lower bends attached to a lower end of the first set of the prongs, a second set of prongs upwardly extending from the second set of the lower bends, a third set of upper bends attached to an upper end of the second set of the prongs, and a third set of prongs downwardly extending from the third set of upper bends.

The base member can include a rear U-shaped base with an upwardly extending left leg and an upwardly extending right leg.

The third set of outer prongs can each include angled cut ends.

The clip holder can have a height of approximately 1 and ⅞ inches and have a width of approximately 1 and ½ inches. The first set of bends can each have a curved bend of approximately ⅛ inch in diameter. The second set of bends can each have a curved bend of approximately 3/16 inch in diameter. The third set of bends can each have a curved bend of approximately ¼ inch in diameter.

The clip holder can be formed from a single elongated vinyl coated wire and have an overall length of approximately 13 inches.

A method of securing elongated lines and supporting the lines on clothing, can include the steps of providing a clothing item having at least one exterior edge, providing an elongated line, providing a clip holder with a base and a plurality of different sets of bends, securing the elongated line in one set of bends of the clip holder, and draping the clip holder on the exterior edge of the clothing with another set of bends of the clip, so that the elongated line is securely supported on the clothing edge.

The clothing exterior edge can include a belt or waist band. The clothing exterior edge can include a shirt pocket. The clothing exterior edge can include a pants pocket. The clothing exterior edge can include a front longitudinal edge on a shirt.

The elongated line can include a medical oxygen line. The elongated line can include an earphone or headset wire line. The elongated line can include a power cord line that can be attached to a power tool or other electrical device, and the like.

The steps of securing and draping steps can include the steps of narrowing and enlarging the different sets of bends by pressing and pulling against prong type portions of the clip holder.

A novel clip holder for securing elongated lines to clothing, can include a base formed from a wire, and a plurality different sets of different diameter bends extending from the base, wherein one set of bends is adaptable to attach about an edge of a clothing item, and another different diameter set of bends is adaptable to secure an elongated line therethrough. The clip holder can be formed from a single elongated vinyl coated wire.

Further objects and advantages of this invention will be apparent from the following detailed description of the presently preferred embodiments which are illustrated schematically in the accompanying drawings.

BRIEF DESCRIPTION OF THE FIGURES

FIG. 2A is a left side view of the novel clip holder of FIG. 1 along arrow 2A.

FIG. 2B is a right side view of the novel clip holder of FIG. 1 along arrow 2B.

FIG. 2C is a rear view of the novel clip holder of FIG. 2A along arrow 2C.

FIG. 2D is a front view of the novel clip holder of FIG. 2A along arrow 2D.

FIG. 3A is a perspective view of the novel clip holder of FIG. 1 holding a medical oxygen line.

FIG. 3B is a perspective view of the novel clip holder of FIG. 1 holding an earphone or headset wire.

FIG. 3C is a perspective view of the novel clip holder of FIG. 1 holding a cord.

FIG. 6 shows the novel clip holder of FIG. 3A with medical oxygen line clipped to the front of a shirt.

FIG. 7 shows the novel clip holder of FIG. 3A with medical oxygen line clipped to a pants pocket.

FIG. 8 shows the novel clip holder of FIG. 3B with earphone or headset wire line clipped to a belt.

FIG. 9 shows the novel clip holder of FIG. 3C with power cord line clipped to a pants pocket.

FIG. 10 is another view of the clip holder of FIG. 2A showing front prong angled end being adjustably bent outward.

FIG. 11 is another view of the clip holder of FIG. 2A showing the second and third set of prongs being adjustably bent outward.

DESCRIPTION OF THE PREFERRED EMBODIMENTS

Before explaining the disclosed embodiments of the present invention in detail it is to be understood that the invention is not limited in its applications to the details of the particular arrangements shown since the invention is capable of other embodiments. Also, the terminology used herein is for the purpose of description and not of limitation.

Figure 1:
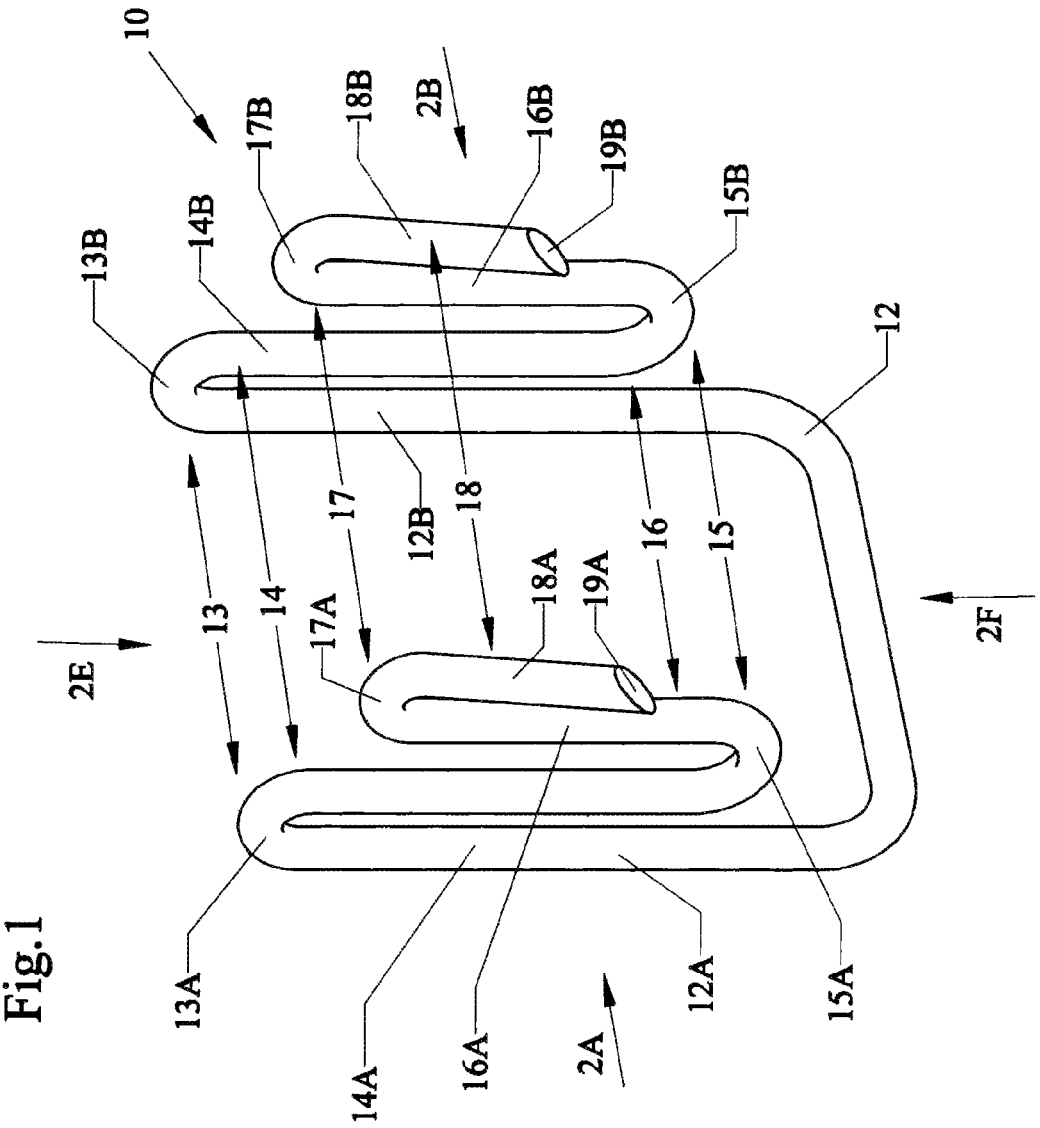
FIG. 1 is a front perspective view of the novel clip holder.
Figure 2F:
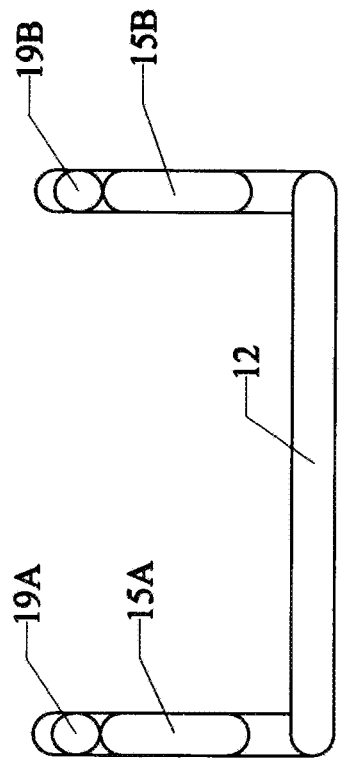
FIG. 2F is a bottom view of the novel clip holder of FIG. 1 along arrow 2F.
Figure 2E:
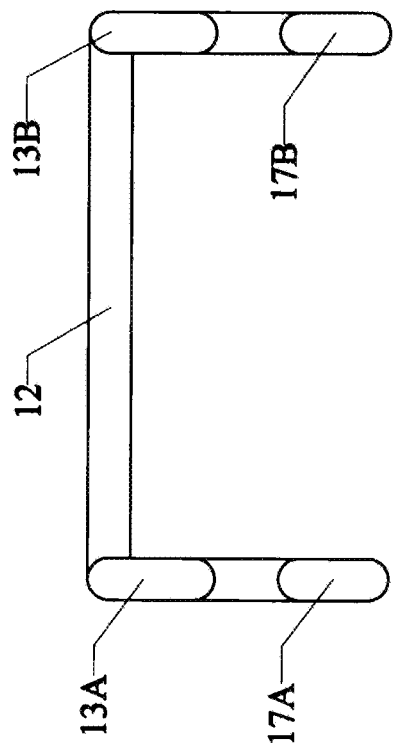
FIG. 2E is a top view of the novel clip holder of FIG. 1 along arrow 2E.

A list of components will now be described.
10. clip holder
12. rear U-shaped base
12A. left base leg
12B. right base leg
13. first bends (upper bends)
13A. left upper first bend
13B. right upper first bend
14. first set of (downwardly) extending prongs
14A. left first downwardly extending prong
14B. right first downwardly extending prong
15. second bends (lower bends)
15A. left second lower bend
15B. right second lower bend
16. second set of (upwardly) extending prongs
16A. left upwardly second extending prong
16B. right upwardly second extending prong
17. third bends (upper bends)
17A. left upper third bend
17B. right upper third bend
18. third set of (downwardly) extending front prongs.
18A. left downwardly extending prong
18B. right downwardly extending prong
19A Angled front left prong end
19B. Angled front right prong end
20. patient/user of clip holder
30. medical oxygen line
40. headset and earphone wire line
50. cord line
60. front of shirt edge
70. shirt pocket
80. belt or waist band
90. pants pocket FIG. 1 is a front perspective view of the novel clip holder 10. FIG. 2A is a left side view of the novel clip holder 10 of FIG. 1 along arrow 2A. FIG. 2B is a right side view of the novel clip holder 10 of FIG. 1 along arrow 2B. FIG. 2C is a rear view of the novel clip holder 10 of FIG. 2A along arrow 2C. FIG. 2D is a front view of the novel clip holder 10 of FIG. 2A along arrow 2D. FIG. 2E is a top view of the novel clip holder 10 of FIG. 1 along arrow 2E. FIG. 2F is a bottom view of the novel clip holder 10 of FIG. 1 along arrow 2F.

Referring to FIGS. 1-2F, the novel clip holder can include rear U-shaped base 12 with left base leg 12A and right base leg 12B, first set of bends 13 (upper bends) with left upper first bend 13A and right upper first bend 13B, a first set of (downwardly) extending prongs 14 with left first downwardly extending prong 14A and right first downwardly extending prong 14B, second set of bends 15 with left second lower bend 15A and right second lower bend 15B, second set of (upwardly) extending prongs 16 with left upwardly second extending prong 16A and right upwardly extending prong 16B, third set of bends (upper bends) 17 with left upper third bend and right upper third bend, third set of (downwardly extending front prongs 18 with left downwardly extending prong 18A and right downwardly extending prong 18B, and angled front left prong end 19A and angled front right prong end 19B.

The novel clip holder 10 can have a height of approximately 1 and 7⁄8 inches between the bottom of the U-shaped base 12 and the first bends 13, and have a width of approximately 1 and 1⁄2 inches between the left base leg/left prongs and the right base leg/right prongs. The novel clip holder can have first set of bends 13, each bend 13A, 13B with an approximately 1⁄8 inch diameter bend at the top, a second set of bends 15, each bend 15A, 15B with an approximately 3⁄16 inch diameter curve bend at the bottom, and a third second of bends 17 each bend 17A, 17B with an approximately 1⁄4 inch bend. The outer ends 19A, 19B can be angled cut at approximately 45 degrees and burred smooth.

The novel clip holder 10 can be formed from coated metal and the like, and formed from a single approximately 13 inch long and approximately 1⁄8 inch diameter green vinyl coated, multi-purpose steel wire. This wire was determined to work well because it cold bends extremely well, no painting is necessary, no welding is necessary, and no heating is needed. The approximately 13 inch long wire forms an adjustable novel clip holder 10. Mass production of the novel clip holders can be done by computer operation using robotic production lines. The wire is obtainable in large rolls making overall production fast and simple.

FIG. 3A is a perspective view of the novel clip holder of FIG. 1 holding a medical oxygen line 30 through the second set of bends 15 so that the left bend 15A and the right bend 15B each grab and securely support and hold, but not pinch about the medical oxygen line 30. The oxygen line 30 can be fit into the curved bends 15 of the two wire clip holder bends 15A, 15B and can be adjusted with ease and moved to the left and to the right by sliding the oxygen line 30 as needed. The adjacent prongs 14, 16 can be bent toward each other or away from each other as needed to securely support the line 30.

FIG. 3B is a perspective view of the novel clip holder of FIG. 1 holding an earphone or headset wire 40 fit between ends 19A, 19B and prongs 16 so to be pinched therebetween and securely and firmly held in place. Alternatively, the wire 40 can be loosely fit into a third set of narrow upper bends 17 so that the left bend 17A and right bend 17B each grab about and support and hold, about an earphone or headset wire line 40. The wire line 40 can pass through and adjusted with ease by moved to the left and to the right as needed. The adjacent prongs 16, 18 can be bent toward each other or away from each other as needed to securely support the wire 40.

FIG. 3C is a perspective view of the novel clip holder of FIG. 1 holding a power type cord 50 through the second set of bends 15 so that the left bend 15A and the right bend 15B each grab and securely support and hold, about a power cord line 50. The cord can be slid to the left or to the right in the bends 15A, 15B. The adjacent prongs 14, 16 can be bent toward each other or away from each other as needed to securely support the cord 50.

Figure 4:
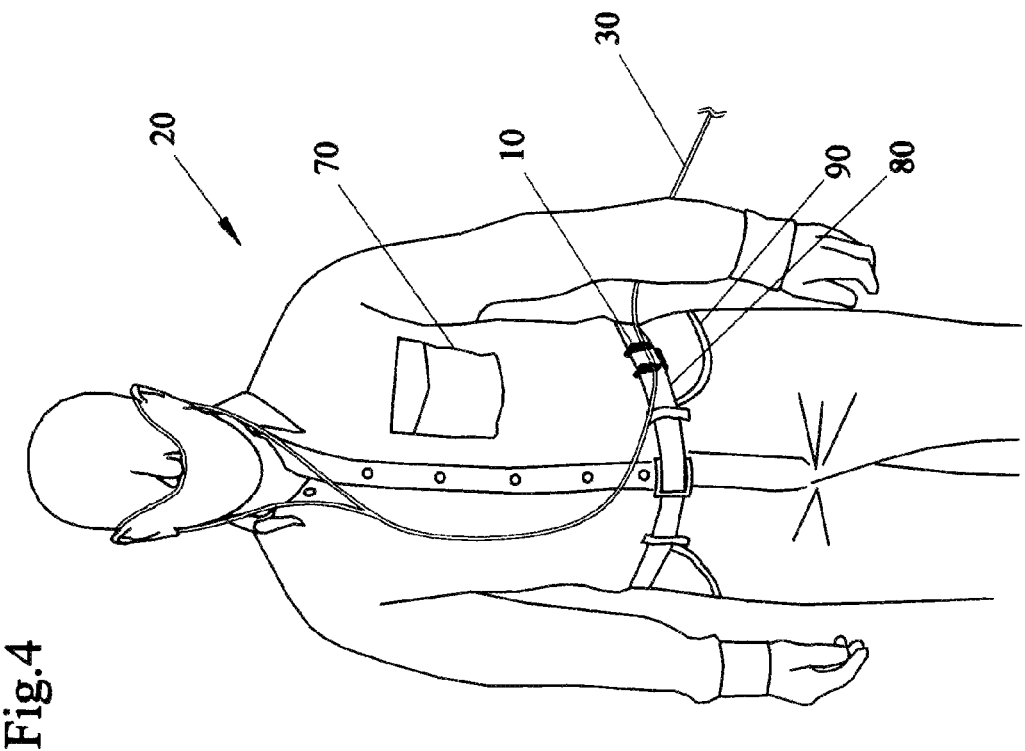
FIG. 4 shows the novel clip holder of FIG. 3A with medical oxygen line clipped to a belt.

FIG. 4 shows the novel clip holder 10 of FIG. 3A with a patient 20 having a medical oxygen line 30 from a nose and ears' supported cannula clipped to a belt 80. The rear U-shaped base 12 with left base legs 12A, 12B shown in the previous figures can be inserted over the inside of the belt 80 with first set of bends 13 on top of the belt 80.

Figure 5:
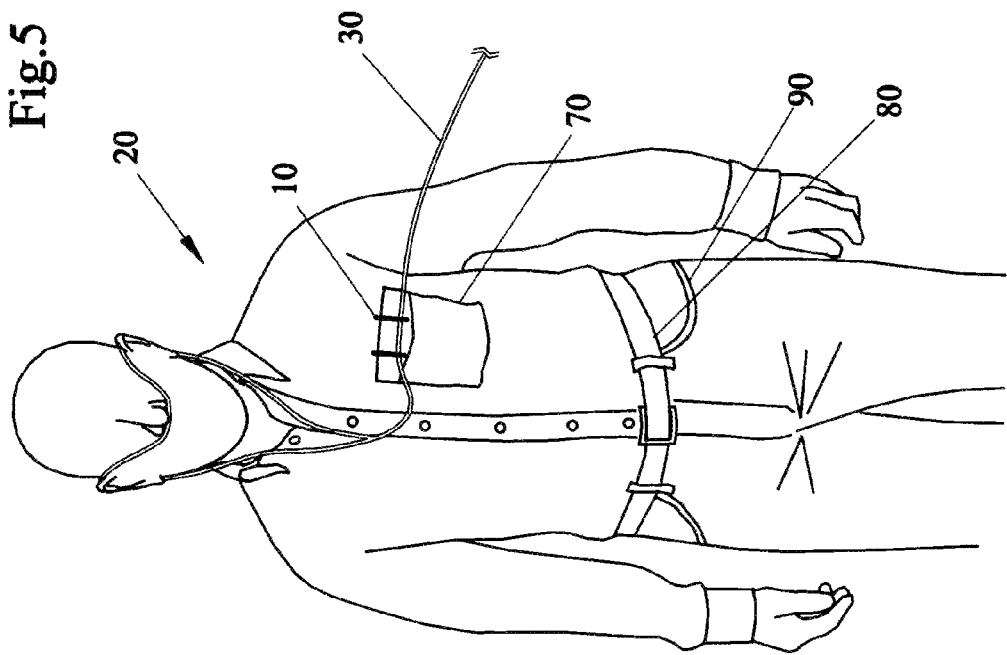
FIG. 5 shows the novel clip holder of FIG. 3A with medical oxygen line clipped to a shirt pocket.

FIG. 5 shows the novel clip holder 10 of FIG. 3A with a patient 20 having a medical oxygen line 30 from a nose and ears' supported cannula clipped to a shirt pocket 70. The rear U-shaped base 12 with left base legs 12A, 12B shown in the previous figures can be inserted over and into the shirt pocket 70 with first set of bends 13 on top of the shirt pocket 70.

FIG. 6 shows the novel clip holder 10 of FIG. 3A with a patient 20 having a medical oxygen line 30 from a nose and ears' supported cannula clipped to the front edge 60 of a shirt. The rear U-shaped base 12 with left base legs 12A, 12B shown in the previous figures can be inserted inside of the front edge 60 of the shirt with first set of bends 13 on the front edge 60 of the shirt.

FIG. 7 shows the novel clip holder 10 of FIG. 3A with a patient 20 having a medical oxygen line 30 from a nose and ears' supported cannula clipped to a pants pocket 90. The rear U-shaped base 12 with left base legs 12A, 12B shown in the previous figures can be inserted into the pants pocket 90 with first set of bends 13 on top of the upper edge of the pants pocket 90.

FIG. 8 shows the novel clip holder 10 of FIG. 3B with a user 20 wearing earphone or headset with wire line 40 clipped to a belt 80. Similarly, the novel clip holder 10 can also be clipped to front edge of a shirt 60, front shirts pocket 70, and front pocket 90.

FIG. 9 shows the novel clip holder 10 of FIG. 3C with a user supporting and holding a power cord line 50 that can be attached to a powered tool, device, and the like such as but not limited to a drill, saw, power screw driver, and the like, also clipped to a belt 80. Similarly, the novel clip holder 10 can also be clipped to front edge of a shirt 60, front shirts pocket 70, and front pocket 90.

Adjustments in tension on belts, waist bands, pockets, clothing edges and the actual conduit lines 30, 40, 50 can be made by using the thumb and index finger to press the clip prongs and legs together or apart as needed.

FIG. 10 is another view of the clip holder 10 of FIG. 2A showing front prong angled end 19A being adjustably bent outward to another position 19A', which changes the diameter of the upper third bend 17A to a larger diameter bend 17A'.

FIG. 11 is another view of the clip holder 10 of FIG. 2A showing the second set of prongs 16(16A) and third set of prongs 18(18A) being adjustably bent outward which changes the diameter of the second set of lower bends 15(15A) to a larger diameter bend 15N.

Although the embodiments describe attaching the clip holders to shirts and pants, and belts, the clip holders can be attached to other clothing items, such as but not limited to caps, jackets, dresses, shorts, and the like. Additionally, the clip holders can be attached to other types of bands such as but not limited to arm bands, wrist bands, sweat bands, and the like.

While the invention describes using one type of colored plastic, the invention can be done in different colors as needed, such as but not limited to white, red, and the like, and combinations thereof.

Although the preferred embodiment describes using wire that has a memory to keep the modified bends in place, the invention can be formed from other materials such as molded plastic and the like. A plastic version can be based on an elongated rectangular sheet of plastic which is either heated or further molded into the overall shapes of the base and different diameter bends of the preceding embodiment. Instead of having pairs of upwardly and downwardly extending prongs, the plastic version would have planar sheet portions in place of the pairs of prongs with the respective bends. The overall configuration would be similar in appearance to the preceding embodiment.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A clip holder for holding and securely supporting elongated lines, comprising:
   a base member having a generally flat front face side and a generally flat rear face side, and having an upper end and a lower end and a length between the upper end and the lower end;
   a first set of upper bends attached to the upper end of the base member;
   a first set of prongs downwardly extending from the first set of upper bends, the first set of prongs having a length greater than at least half the length of the length between the upper end and the lower end of the base member,
   a second set of lower bends attached to a lower end of the first set of the prongs;
   a second set of prongs upwardly extending from the second set of the lower bends, the second set of prongs having a length greater than at least half the length of the first set of prongs;
   a third set of upper bends attached to an upper end of the second set of the prongs; and
   a third set of prongs downwardly extending from the third set of upper bends, the third set of prongs having a length greater than at least half the length of the second set of prongs.

2. The clip holder of claim 1, wherein the base member includes:
   a rear U-shaped base with an upwardly extending left leg and an upwardly extending right leg.

3. The clip holder of claim 1, wherein the third set of prongs each include:
    outer ends each having an angled cut at approximately 45 degrees.

4. The clip holder of claim 1, wherein the clip holder includes a height of approximately 1 and ⅞ inches and have a width of approximately 1 and ½ inches.

5. The clip holder of claim 1, wherein the first set of bends each have a curved bend of approximately ⅛ inch in diameter.

6. The clip holder of claim 5, wherein the second set of bends each have a curved bend of approximately 3/16 inch in diameter.

7. The clip holder of claim 6, wherein the third set of bends each have a curved bend of approximately ¼ inch in diameter.

8. The clip holder of claim 1, wherein the clip holder is formed from a single elongated vinyl coated wire.

9. The clip holder of claim 8, wherein the single elongated vinyl coated wire has an overall length of approximately 13 inches.

10. The clip holder of claim 1, wherein the length of the first set of prongs is less than the length between the upper end and the lower end of the base member.

11. The clip holder of claim 10, wherein the length of the second set of prongs is less than the length of the first set of prongs.

12. The clip holder of claim 11, wherein the length of the third set of prongs is less than the length of the second set of prongs.

13. A clip holder for holding and securely supporting elongated lines, comprising:
    a rear base member having a U-shaped base with an upwardly extending left leg and an upwardly extending right leg, each of the left leg and the right leg having a length, wherein both the U-shaped base and the upwardly extending left leg and upwardly extending right leg have a flat rear face side and a flat front face side;
    a first set of upper bends attached to upper ends of the left leg and the right leg, the first set of upper bends extending from the flat front face side of the rear base member;
    a first set of prongs downwardly extending from the first set of upper bends, the first set of prongs having a length greater than at least half the length of the length between the U-shaped base and the upper ends of the left leg and the right leg, and being less than the length between the U-shaped base and the upper ends of the left leg and the right leg;
    a second set of lower bends attached to a lower end of the first set of the prongs,
    a second set of prongs upwardly extending from the second set of the lower bends, the second set of prongs having a length greater than at least half the length of the first set of prongs, and less than the length of the first set of prongs;
    a third set of upper bends attached to an upper end of the second set of the prongs; and
    a third set of prongs downwardly extending from the third set of upper bends, the third set of prongs having a length greater than at least half the length of the second set of prongs, and less than the length of the second set of prongs, and wherein the clip holder is formed from a single elongated vinyl coated wire having an overall length of approximately 13 inches.

14. The clip holder of claim 13, wherein the clip holder includes a height of approximately 1 and ⅞ inches and have a width of approximately 1 and ½ inches.

15. The clip holder of claim 13, wherein the first set of bends each have a curved bend of approximately ⅛ inch in diameter.

16. The clip holder of claim 15, wherein the second set of bends each have a curved bend of approximately 3/16 inch in diameter.

17. The clip holder of claim 16, wherein the third set of bends each have a curved bend of approximately ¼ inch in diameter.

18. The clip holder of claim 13, wherein the clip holder is formed from a single elongated vinyl coated wire strand.

19. A clip holder for holding and securely supporting elongated lines, comprising:
    a base member having an upper end and a lower;
    a first set of upper bends attached to the upper end of the base member, wherein the first set of bends each have a curved bend of approximately ⅛ inch in diameter;
    a first set of prongs downwardly extending from the first set of upper bends;
    a second set of lower bends attached to a lower end of the first set of the prongs, wherein the second set of bends each have a curved bend of approximately 3/16 inch in diameter;
    a second set of prongs upwardly extending from the second set of the lower bends;
    a third set of upper bends attached to an upper end of the second set of the prongs, wherein the third set of bends each have a curved bend of approximately ¼ inch in diameter; and
    a third set of prongs downwardly extending from the third set of upper bends, wherein the clip holder includes a height of approximately 1 and ⅞ inches and have a width of approximately 1 and ½ inches.

\* \* \* \* \*